United States Patent [19]

Ito et al.

[11] Patent Number: 5,026,959
[45] Date of Patent: Jun. 25, 1991

[54] MICROWAVE RADIATOR FOR WARMING THERAPY

[75] Inventors: Koichi Ito, Chiba; Motomu Matsunaga, Kawasaki; Satoru Kurokawa, Chiba; Koji Ueno, Funabashi, all of Japan

[73] Assignee: Tokyo Keiki Co. Ltd., Tokyo, Japan

[21] Appl. No.: 423,753

[22] Filed: Oct. 18, 1989

[30] Foreign Application Priority Data

Nov. 16, 1988 [JP] Japan ................................ 63-289670
Mar. 24, 1989 [JP] Japan ................................ 1-33649[U]

[51] Int. Cl.$^5$ .......................... H05B 6/72; H05B 6/80
[52] U.S. Cl. .................... 219/10.55 A; 219/10.55 F; 219/10.81; 128/401; 128/784; 128/804
[58] Field of Search ................ 219/10.55 A, 10.55 R, 219/10.55 F, 10.81; 128/399, 401, 783, 784, 804; 333/237; 343/770, 769, 768

[56] References Cited

U.S. PATENT DOCUMENTS

| | | | |
|---|---|---|---|
| 3,230,957 | 1/1966 | Seifert | 128/804 |
| 4,743,725 | 5/1988 | Risman | 219/10.55 F |
| 4,823,811 | 4/1989 | Harrison | 128/804 |
| 4,825,880 | 5/1989 | Stauffer et al. | 128/804 |
| 4,841,988 | 6/1989 | Fetter et al. | 128/804 |

FOREIGN PATENT DOCUMENTS 61-33961 10/1986 Japan .

OTHER PUBLICATIONS

English language abstract of Japanese Utility Model Unexamined Publication No. 61-33961, published 10/3/86.

*Primary Examiner*—Philip H. Leung
*Attorney, Agent, or Firm*—Sandler, Greenblum & Bernstein

[57] ABSTRACT

This invention relates to a microwave radiator for warming therapy inserted into a human body to cure focuses of the body such as tumors. It has a first and second high-frequency coaxial cable. The second high-frequency coaxial cable has an inner conductor and a plurality of ring conductors disposed at the outer periphery of the inner conductor via a dielectric. The second high-frequency coaxial cable is inserted into the focuses of the body, and warming therapy can be conducted using radiated electromagnetic waves.

17 Claims, 7 Drawing Sheets

MICROWAVE RADIATOR FOR WARMING THERAPY

BACKGROUND OF THE INVENTION

1. Field of the Invention

The present invention relates to a microwave radiator for warming therapy, particularly, to a microwave radiator for warming therapy directly inserted into an affected part.

2. Description of the Prior Art

This kind of applicator for warming therapy has been previously developed as is shown in Prior Art FIG. 14 (1) (2) and, Prior Art FIG. 15 (1) (2).

An example of the conventional art, shown in FIG. 14 (1), is of the same kind as a monopole antenna, and is constructed similarly to an applicator in which the outer conductors in the tips of the coaxial cables are removed. More specifically, it has a central conductor 40, and an outer conductor 42 provided around a dielectric 41. The tip of the outer conductor 42 is removed a distance equal to the predetermined length of an A part.

This kind of applicator for warming therapy, as shown in FIG. 14 (2), has the skirt 43 added to it, the base end of which is short-circuited. This prevents a current from flowing on the surface of the conductor of the coaxial cables, thereby stopping overheating of the normal tissues of a human body in the vicinity of the conductor.

The example of a conventional applicator shown in FIG. 15 (1) is characterized in that a band-like conductor 50 is wound helically around the outer surface of the dielectric 41 of the example of the conventional applicator shown in FIG. 14 (1) described above, and thus a helical slit 51 is formed.

The example of the conventional applicator shown in FIG. 15 (1) is disclosed, for example, in Japanese Utility Model Unexamined Publication No. 61-33961 as being a body cavity insertion type. The applicator of this Japanese Utility Model Unexamined Publication No. 61-33961 can be used for inserting into the tissues of a focus and for warming it by making it smaller.

However, the above described example of the conventional applicator has significant disadvantages concerning the function of warming the focuses.

This disadvantage will be concretely described below.

First, in the examples of the conventional applicators shown in FIG. 14 (1) (2) and FIG. 15 (1) (2), the length A of the central conductor protruding from the coaxial cable B is basically a wavelength about ¼ the frequency in use. More specifically, when the frequency to be used in the muscular tissues of a human body is set to 400 MHz, the following lengths are needed: 2.0 cm at 400 MHz, 5.5 cm at 100 MHz, and 8.5 cm at 60 MHz. When the length is shorter than these, the input impedance matching becomes poor, and radiation efficiency weakens.

On the other hand, in the warming therapy, it is desirable to be able to warm and cure an extensively affected part with one microwave radiator. This is important from the viewpoint of softening the pain of a patient, caused by many microwave radiators being inserted into the body.

By the way, the tissues of the body can be handled as a kind of dielectric-lost material including tissues of a malignant tumor. For this reason, in the case of electromagnetic waves, the lower their frequencies are, the better osmotic permeability they have.

For example, when microwaves are radiated and propagated from the surface of the body to the muscular tissues, the osmotic depth at which the power is reduced by half is as follows: about 1.0 cm at 400 MHz, about 1.4 cm at 200 MHz, about 2.2 cm at 100 MHz, and about 3.0 cm at 60 MHz. This indicates that in the warming therapy in which those applicators shown in FIG. 14 (1) (2) are used, the frequency need be selected depending on the depth from the surface of the body.

Therefore, the selection of the frequency to be used is irrespective of the extent of the affected part in the horizontal direction.

For this reason, for an affected part which is flat and extending in the horizontal direction, an applicator that operates at a high frequency must be used. Since high frequency microwaves have a poor osmotic permeability for tissues, many microwave radiators are needed. This led to inconveniences such that patients suffer much pain from the many insertions.

The applicator of FIG. 15 (1) is, originally, of the body cavity insertion type, and can also be used as an insertion type as described above.

The applicator of FIG. 15 (1) is one in which a consecutive helical slit 51 is provided on the outer conductor 42 of a high-frequency coaxial cable or equivalent, and its tip is short-circuited to the inner conductor 40.

The objective of the microwave radiator shown in FIG. 15 (1) is to warm by means of leak waves from a helical slit 51. However, actually, it does not operate in such a way.

That is, the helical slit 51 provided in a very thin coaxial cable for high frequency as compared with its wavelength results from forming a helical antenna, whose length of one helical winding is very short.

It is generally well known that this helical antenna does hardly match coaxial cable and radiation efficiency is poor.

In this case, the inner conductor of a high-frequency coaxial cable lies at the position of the helical axis, so this structure causes even waves whose phase speed is very close to the light speed ($3 \times 10^8$ m/sec) to propagate. That is, the surface waves propagate. In this structure, the input impedance matching is improved to some extent, as compared with the case of only a very small helical antenna compared with the above described wavelength. The reason is that the presence of the inner conductor serves as a surface wave transmission path. However, this surface wave weakens rapidly away from the axis (the inner conductor) of the transmission path (see FIG. 15 (2)). For this reason, the warming area is limited to the transmission path, i.e., the area most close to the microwave radiator. For this reason, the example of the conventional art shown in FIG. 15 (1) is limited to the applicator having the same effect as that shown in FIG. 14 (1) (2).

SUMMARY OF THE INVENTION

It is an object of the present invention to solve the disadvantages of the example of the conventional art, and particularly, to provide a microwave radiator for warming therapy, capable of making an electromagnetic energy penetrate widely into focuses and exerting no adverse influence to the normal tissues.

To attain the above described objects, the microwave radiator of the present invention comprises an inner conductor extending axially, a first high-frequency coaxial cable provided around the inner conductor via a dielectric and having an outer conductor extending concentrically to said inner conductor, and a second high-frequency coaxial cable in which a ring conductor is mounted around the dielectric at a predetermined space along the axial direction, said inner conductor and dielectric of which are extended on the extending line of the first high-frequency coaxial cable.

The relative distance between said ring conductors can be set to an equal space or different space, and each width is the same or can be made smaller gradually toward the tip side of the second high-frequency coaxial cable.

Current blocking means should preferably be provided around the first high-frequency coaxial cable, then overheating of the normal tissues of a human body can be prevented by the function of the current blocking means.

BRIEF DESCRIPTION OF THE INVENTION

FIGS. 14(1), 14(2), 15(1), 15(2) are, respectively, explanation diagrams illustrating the examples of the conventional applicators.

DETAILED DESCRIPTION OF THE PREFERRED EMBODIMENTS

One embodiment of the present invention will be explained below with reference to FIGS. 1 and 3.

Figure 1:
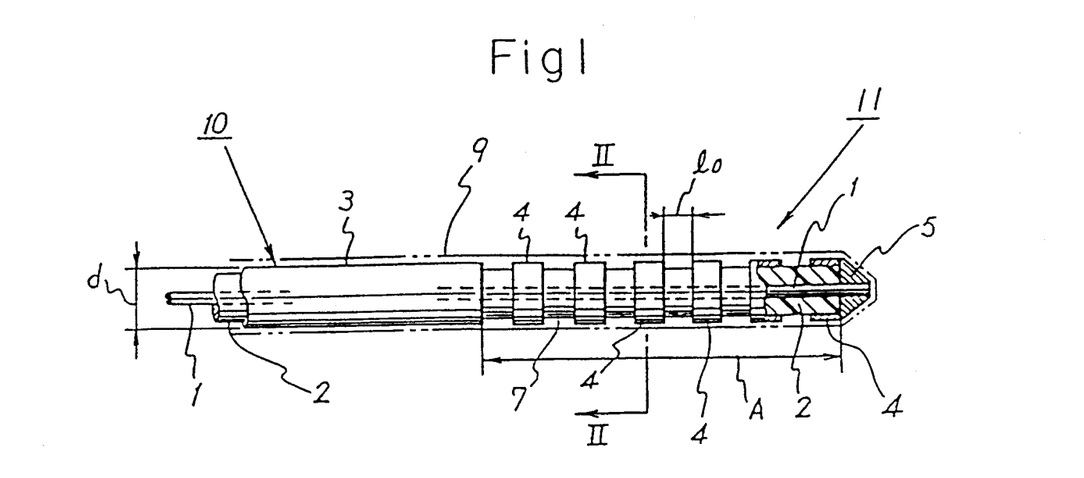
FIG. 1 is a front elevation partly in cross section illustrating one embodiment of the present invention.

The embodiment shown in FIG. 1 has a relatively thin first high-frequency coaxial cable formed of a relatively thin inner conductor 1 and an outer conductor 3 disposed around the inner conductor 1 via the dielectric 2.

On the extension line of the first high-frequency coaxial cable 10 are extendedly provided the inner conductor 1 and the dielectric 2. A plurality of ring conductors 4, 4, - - - are provided around the surface of the extended dielectric 2 at a predetermined spacing, thus forming a second high-frequency coaxial cable 11. The symbol $l_o$ indicates the clearance distance (slit width) between the ring conductors 4.

Figure 2:
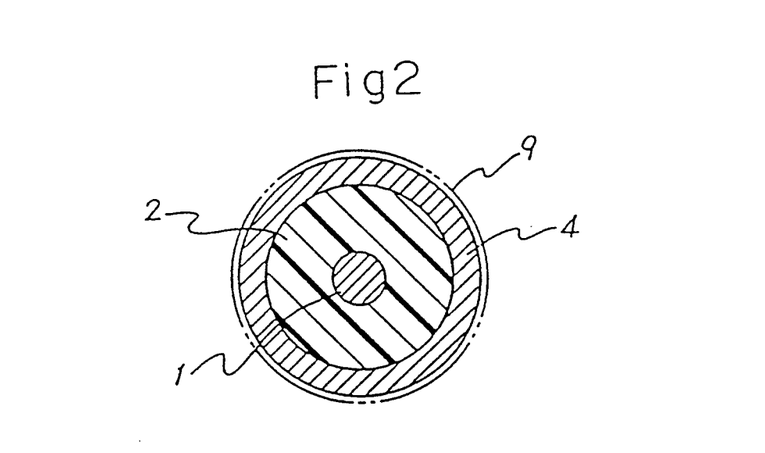
FIG. 2 is a cross section taken on line II—II of FIG. 1.

Further, a conductance member on said cap 5 is mounted between the ring conductors 4 situated in the far end part of the above described ring conductors 4 and the inner conductor 1. The reference character 9 indicates a protective film. For this protective film 9, a polymer compound film is used. The reference character d indicates the diameter of the above described outer conductor 3. The diameter d of this outer conductor 3 is, for example, set to 0.5 to 1.0 mm. The length A of the dielectric 2 in the second high-frequency coaxial cable 11 and the relative distance (width of slit 7) between the ring conductors 4 is arranged to be specified in advance in accordance with the frequency to be used. FIG. 2 is a cross section taken along the line II—II of FIG. 1.

The operation of the embodiment shown in FIGS. 1 and 2 will now be explained.

The plurality of the ring conductors 4 form a ring slit array together with the clearance distance $l_o$ between them. Therefore, this ring slit array is represented by the equivalent circuit as shown in FIG. 3.

Figure 3:
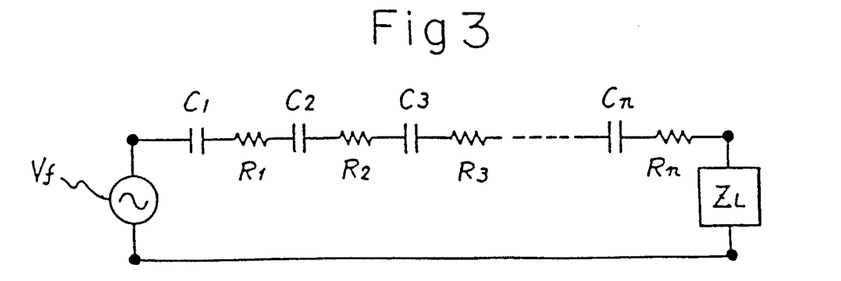
FIG. 3 is a circuit diagram illustrating an equivalent circuit generalized from FIG. 1.

In FIG. 3, $V_f$ indicates a high-frequency voltage applied to the coaxial cable. $C_l$ to $C_n$ indicate an equivalent capacity generated by the operation that a high-frequency current flowing on the outer conductor is shut off by the slit 7 and is converted to a displacement current. $R_l$ to $R_n$ is a radiation resistance that shows the magnitude of the electromagnetic wave radiated by the slit at the same time. $Z_L$ indicates a load mounted in the termination of the slit array. In the case of FIG. 1, this load $Z_L$ is set to 0 Ω by the function of the conduction member or end cap 5.

Next, the concrete operation will be described. The high-frequency voltage applied to the first high-frequency coaxial cable 10 causes a current determined by the characteristic impedance of the cable 10 to develop on the inner and outer conductors 1, 3. As is well known, the transmission mode for transmission to the coaxial cable 10 is the $TEM_l$ mode. This mode causes a current to develop on the outer conductor 3 of the coaxial cable 10 in the direction of its length. Accordingly, this current traverses the ring slit 7 at right angles. At this time, the capacity and radiation efficiency vary according to the width of the slit 7 $l_o$. That is, if the width of the slit 7 $l_o$ is too wide, the second high-frequency coaxial cable 11 becomes open, and if too narrow, the capacity becomes equivalently large. Thus, the slit 7 becomes short-circuited, the radiation efficiency getting closer to 0 Ω.

Therefore, the width of the slit 7 $l_o$ is determined according to the frequency of the electromagnetic wave that excites the slit part.

The embodiment shown in FIG. 1 described above is used with it inserted in the focuses of the body. As described above, therefore, it has a small diameter of 0.5 to 1.0 mm.

The ring slit 7 does not generate the surface wave transmission mode such that an actual current flows along the helical conductor 50 as in a conventional one of FIG. 15 (1) since it cuts off completely the actual current that flows through the ring conductors 4 of the second high-frequency coaxial cable 11. Thus, radiation waves are effectively generated, and the surrounding of the tissues of the body is entirely warmed effectively by the dielectric loss within the tissues of the body.

Another embodiment will now be explained.

Figure 4:
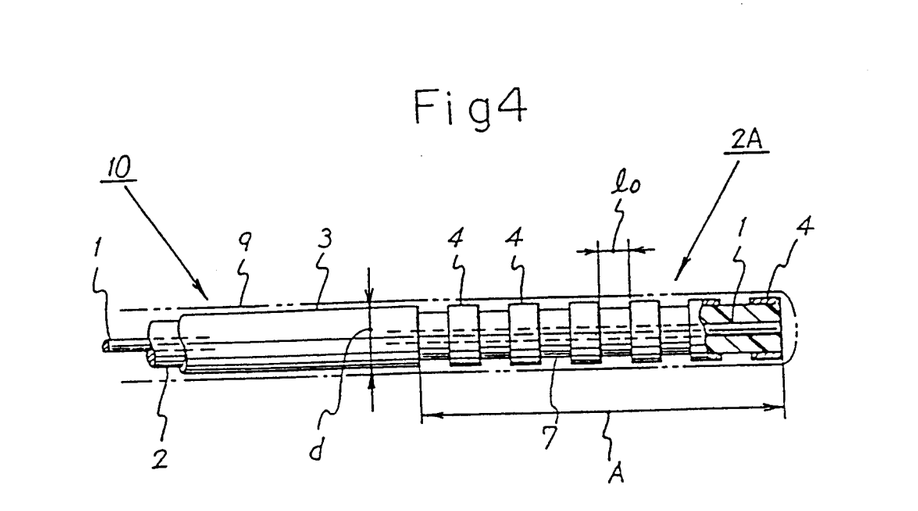
FIGS. 4 to 13 are explanation diagrams illustrating other embodiments respectively.

FIG. 4 shows a case where the conduction member 5 is removed from the embodiment shown in FIG. 1. In this case, the equivalent circuit in FIG. 3 becomes $Z_L \div \infty$. This means that the tip is set to an open state. In this case, the radiation energy is effectively output.

Figure 5:
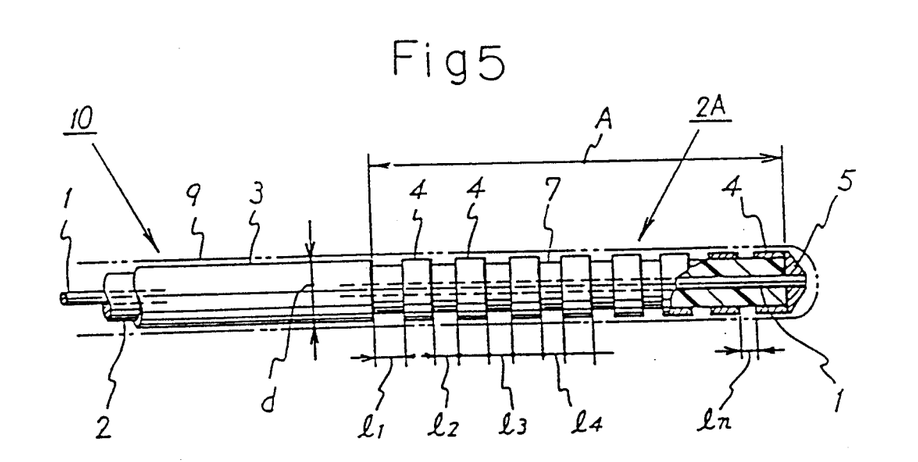

FIG. 5 is characterized in that in the embodiment shown in FIG. 1, the width of the slit $l_o$ is changed in turn, and the following is set: $l_1 \neq l_2 \neq l_3 - - - \neq l_n$.

In this case, as for the ring conductors 4, those having the same width are used.

Figure 6:
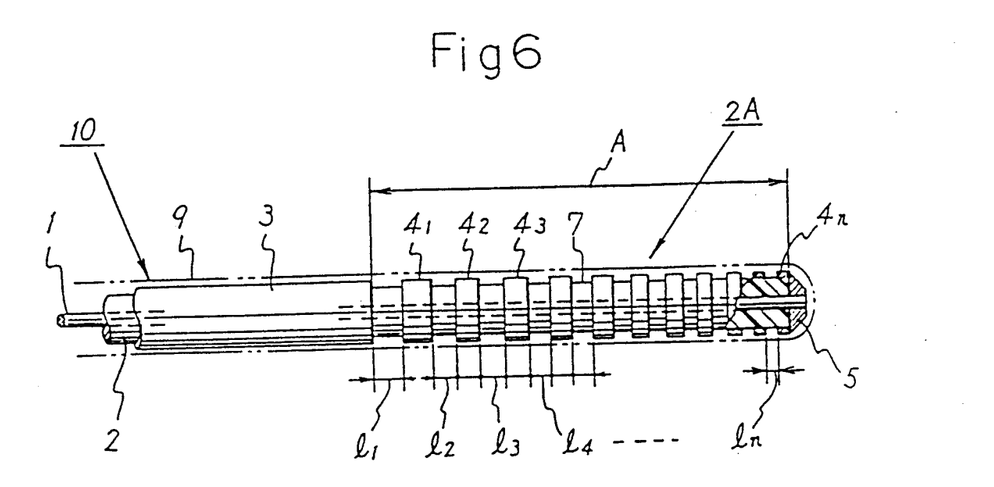

FIG. 6 is characterized in that the width of the slit 7 is changed to $l_1 \neq l_2 \neq l_3 - - - \neq l_n$ in the same way as in FIG. 5 described above, and at the same time the width of the ring conductor is changed as $4_1, 4_2, 4_3, - - -, 4_n$ in accordance with the change of the width of the slit.

In this way, also, it functions the same as in FIG. 1, and there is, in particular, an advantage that the width of the warming depth (warming depth area) can be changed by changing the frequency.

Figure 7:
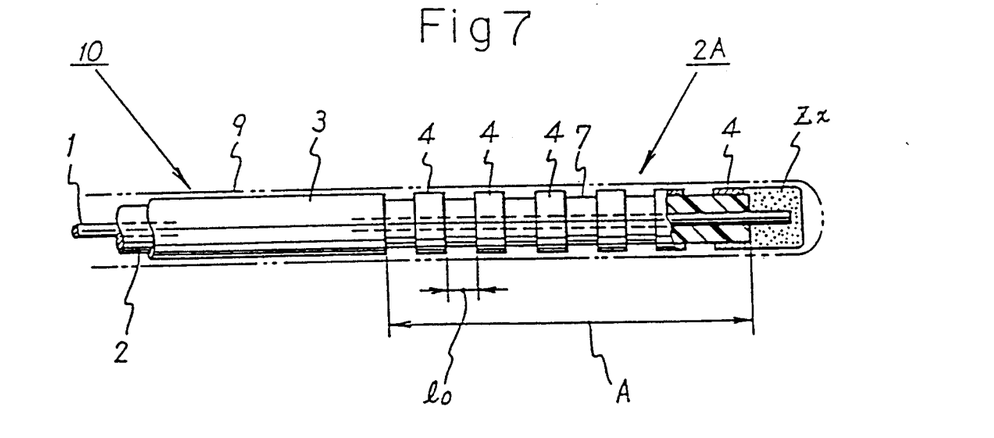

Further, FIG. 7 is characterized in that in the embodiment shown in FIG. 1, the load $Z_x$ having the same impedance value as that of the characteristic impedance which the above described high-frequency coaxial cable 10 has, is mounted.

In this way, no reflection at the termination occurs, thus a microwave radiator having an excellent energy efficiency can be obtained.

Figure 8:
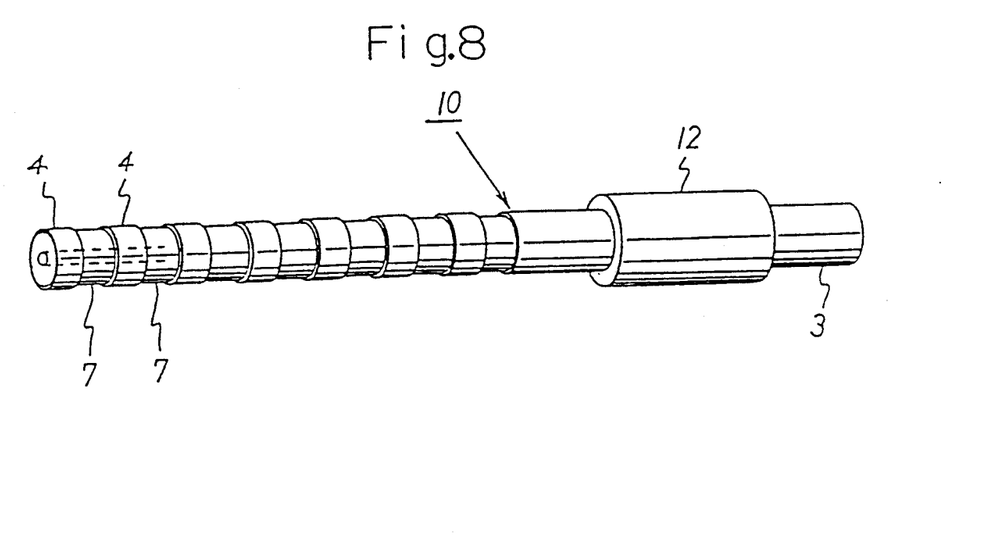
Figure 9:
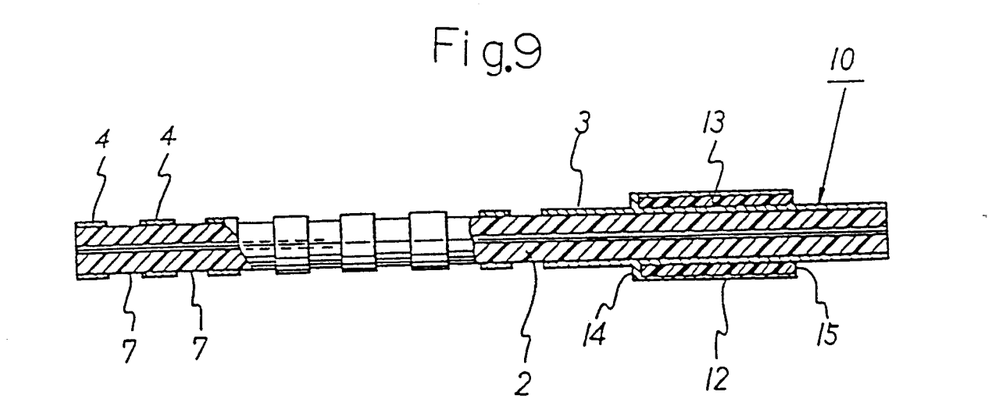

In the embodiments shown in FIG. 8 and 9, the skirt functioning as current blocking means is located around the outer periphery of the conductor 3 in the first high-frequency coaxial cable 10.

This skirt 12 is a ring conductor of the length about ¼ wavelength of the electromagnetic wave in use, and is mounted via an insulator 13. An end face 14 near the ring conductor 4 is structurally short-circuited to the first high-frequency coaxial cable 10. Since the microwave radiator of the present invention is inserted into a human body for use, the diameter of the skirt 12 is set to about not greater than 1.1 mm.

Since the skirt 12 mounted to the outer conductor 3 forms a ¼ wavelength short circuit, its open end face 15 has a high impedance. Accordingly, the skirt 12 has the function of blocking the current flowing along the coaxial cable from the slit 7, at the open end face, and can control the current flowing from this point to the direction of power feed. This skirt has a function as an element forming a desirable current distribution for use in a microwave radiator by adjusting its length, diameter and axial mounting position.

Figure 12:
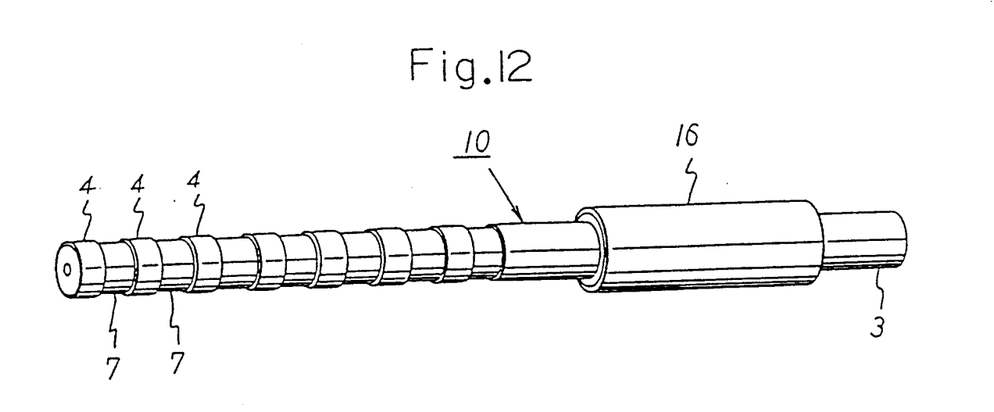
Figure 13:
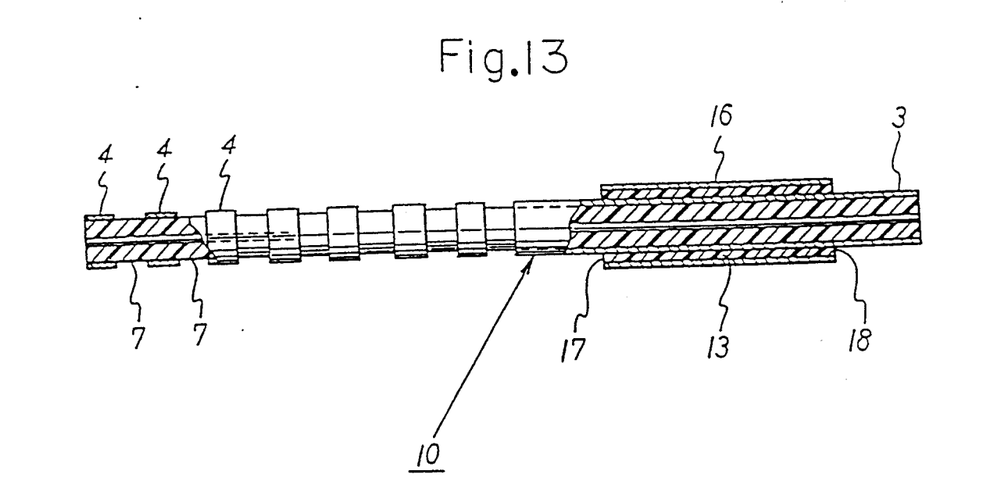
Figure 14:
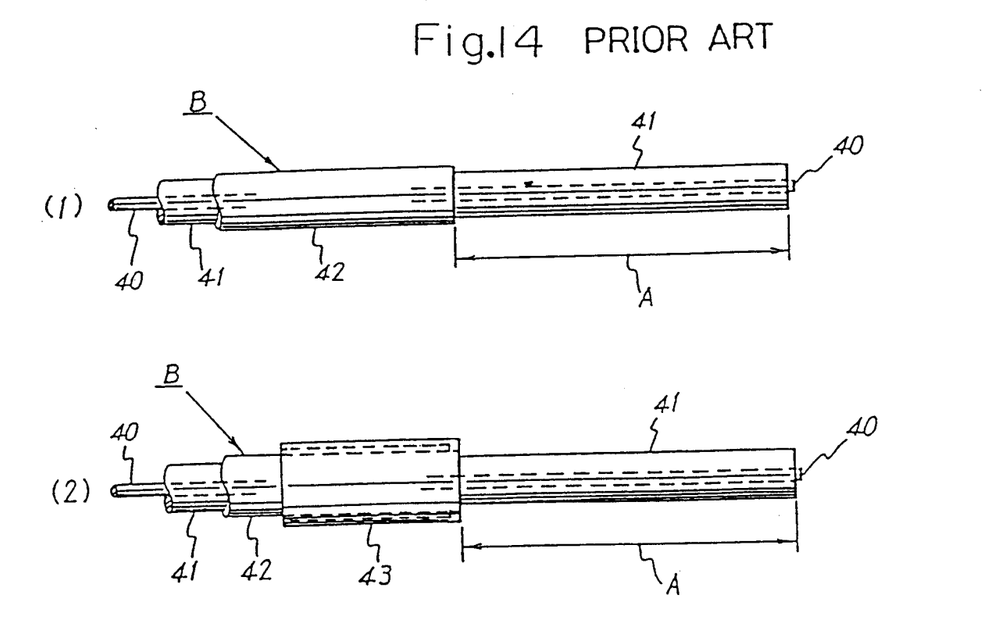
Figure 15:
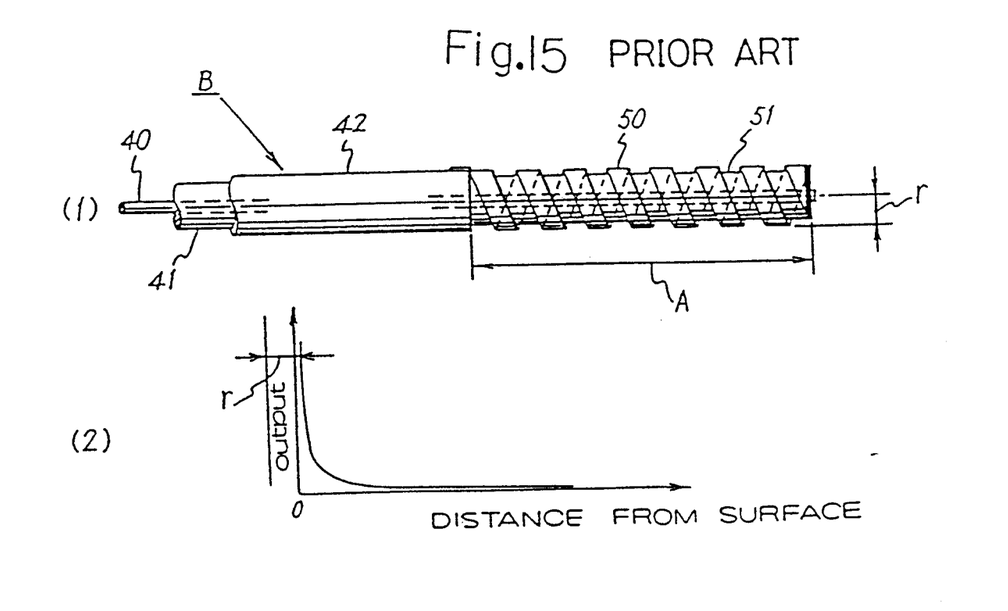

In the skirt 12, the end face 15 near the power feed point may be short-circuited as the embodiments shown in FIGS. 12 and 13.

Figure 10:
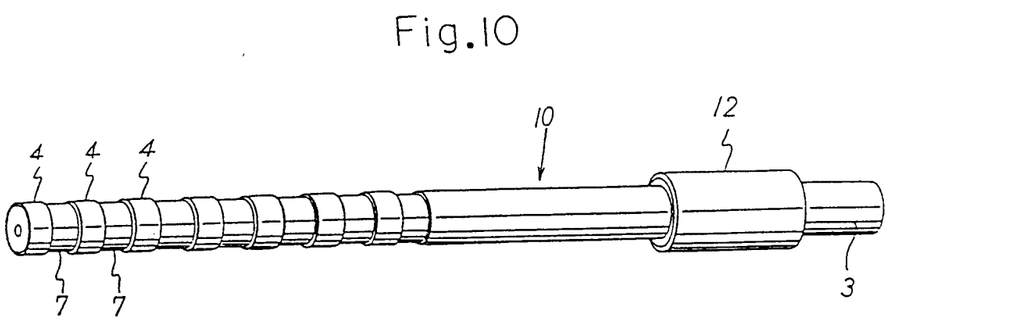
Figure 11:
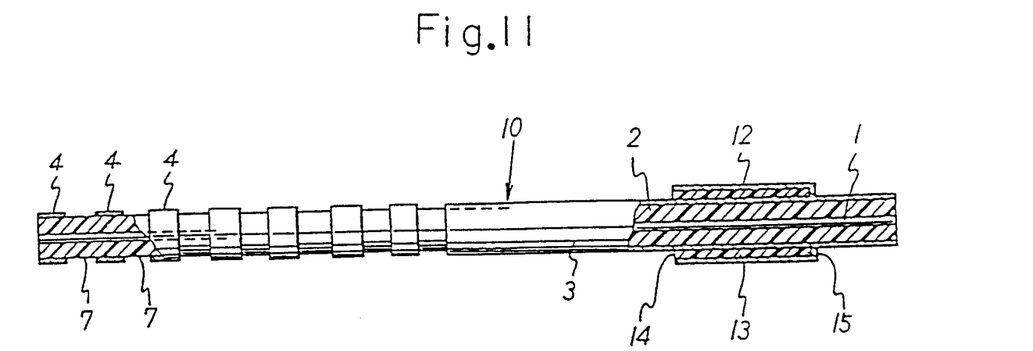

In the embodiment of FIGS. 10 and 11, a sleeve 16 may be located around the outer conductor 3. In this case, the length of the sleeve 16 is set to half the wavelength of the electromagnetic wave in use.

Since the sleeve 16 forms a half-wavelength circuit, both end faces of which are open, the high impedance part of both end faces function to block the current. Thus, the current flowing in the direction of power feed passes two restrain elements, so a new advantage that its magnitude becomes smaller than that of the embodiment having the skirt arises.

A desired current distribution can be formed in the same way as for the above described skirt 12 by adjusting the length, diameter and mounting position of the sleeve 16.

In this embodiment, the sleeve 16 need be short-circuited with the first high-frequency coaxial cable 10, so it becomes simple in structure.

As set forth hereinabove, according to the present invention, the high-frequency current flowing on the outer conductor can be suppressed effectively. This enables the microwave energy to be effectively radiated. Therefore, a microwave radiator, formerly unavailable, such that when the microwave radiator is inserted into the warming place, its surrounding can be effectively warmed over a relatively wide range, can be provided.

The current flowing along the first high-frequency coaxial cable can be blocked to control warming of the normal tissues by the function of the skirt.

A practical microwave radiator for warming therapy, formerly unavailable, such that a current distribution desirable for a microwave radiator can be realized and the frequency band to be used can be widened by adjusting the mounting position and shape of the skirt and the sleeve, can be provided.

What is claimed is:

1. A microwave radiator having an axially extending length, for therapeutic treatment, said radiator comprising:
    an inner conductor extending along the axial length of said radiator;
    a first high frequency coaxial cable, comprising an outer conductor and a portion of said inner conductor, said outer conductor being coaxially disposed about said inner conductor and extending along said portion of said inner conductor;
    a dielectric disposed between said inner conductor and said outer conductor and extending along the entire length of said inner conductor; and
    a second high frequency coaxial cable adjacent to said first coaxial cable, said second coaxial cable having spaced conductive rings disposed around said dielectric along a remaining portion of said inner conductor, whereby electromagnetic radiation may flow in between said rings, in a direction generally perpendicular to said axial length of said inner conductor.

2. A microwave radiator for therapeutic treatment according to claim 1, wherein the distance between adjacent spaced rings is constant.

3. A microwave radiator for therapeutic treatment according to claim 1, wherein the distance between pairs of adjacent rings is not equal.

4. A microwave radiator for therapeutic treatment according to claim 3, wherein the axial width of said rings is constant.

5. A microwave radiator for therapeutic treatment according to claim 1, wherein the distance between pairs of said spaced rings becomes progressively smaller along the longitudinal axis of the said second coaxial cable.

6. A microwave radiator for therapeutic treatment according to claim 1, said radiator further having an end and further comprising an end cap disposed at said end of said radiator and joining said inner conductor with a ring of said second coaxial cable, and a skirt flange surrounding and attached to the outside of said outer conductor of said first coaxial cable.

7. A microwave radiator for warming therapy according to claim 6, wherein said end cap has a characteristic impedance that substantially matches the characteristics impedance of the said first coaxial cable.

8. A microwave radiator for warming therapy according to claim 1, said radiator further having an end and further comprising an end cap disposed at said end of said radiator and joining said inner conductor with a ring of said second high frequency coaxial cable.

9. The microwave radiator for therapeutic treatment according to claim 8, wherein said end cap is a conductor.

10. A microwave radiator having an axially extending length, for therapeutic treatment, said radiator comprising:
    an inner conductor extending along the axial length of said radiator;
    a first high frequency coaxial cable, comprising an outer conductor and a portion of said inner conductor, said outer conductor being coaxially disposed about said inner conductor and extending along said portion of said inner conductor;

a dielectric disposed between said inner conductor and said outer conductor and extending along the entire length of said inner conductor;

a second high frequency coaxial cable adjacent to said first coaxial cable, said second coaxial cable having spaced conductive rings disposed around said dielectric along a remaining portion of said inner conductor, whereby electromagnetic radiation may flow in between said rings in a direction generally perpendicular to the axial direction of said inner conductor; and an end cap disposed at the end of the radiator and joining said inner conductor with a ring of said second high frequency coaxial cable, wherein said end cap has a characteristic frequency value substantially the same as the characteristic impedance value of the first high frequency coaxial cable.

11. A microwave radiator having an axially extending length, for therapeutic treatment, said radiator comprising:

an inner conductor extending along the axial length of said radiator;

a first high frequency coaxial cable, comprising an outer conductor and a portion of said inner conductor, said outer conductor being coaxially disposed about said inner conductor and extending along said portion of said inner conductor;

a dielectric disposed between said inner conductor and said outer conductor and extending along the entire length of said inner conductor;

a second high frequency coaxial cable adjacent to said first coaxial cable, said second coaxial cable having spaced conductive rings disposed about said dielectric along a remaining portion of said inner conductor, whereby electromagnetic radiation may flow in between said rings in a direction generally perpendicular to the axial direction of said inner conductor; and a skirt surrounding said outer conductor of said first high frequency coaxial cable, to alter the current flowing along the radiator.

12. A microwave radiator for therapeutic treatment according to claim 11, wherein the mounting position of the said skirt can be axially adjusted to alter the current flowing in the radiator.

13. A microwave radiator for therapeutic treatment according to claim 11, wherein the diameter of said skirt can be altered to change the current flowing in said radiator.

14. A microwave radiator for therapeutic treatment according to claim 11, wherein said skirt has a length in the axial direction of about ¼ of the wavelength of the electromagnetic wave emitted by the radiator.

15. A microwave radiator for therapeutic treatment according to claim 11, wherein said skirt has a length in the axial direction of about ½ the wavelength of the electromagnetic wave emitted by the radiator.

16. A microwave radiator for therapeutic treatment according to claim 11, wherein said skirt is attached to the outside of said outer conductor.

17. A microwave radiator for therapeutic treatment according to claim 16, wherein said skirt is short-circuited.

* * * * *

UNITED STATES PATENT AND TRADEMARK OFFICE
CERTIFICATE OF CORRECTION

PATENT NO. : 5,026,959

DATED : June 25, 1991

INVENTOR(S) : Koichi ITO et al.

It is certified that error appears in the above-identified patent and that said Letters Patent is hereby corrected as shown below:

At column 1, line 15, delete "," after "and".
At column 2, line 65, change "to the" to ---on---.
At column 3, line 51, change "on said" to ---or end---.
At column 4, line 52, change "$\div\infty$" to ---$\dot{\div}$---.
At column 5, line 33, change "12 and 13" to ---10 and 11---.
At column 5, line 34, change "10 and 11" to ---12 and 13---.
At column 7, line 15 (claim 10, line 25), change "frequency" to ---impedance---.

Signed and Sealed this

Twenty-third Day of March, 1993

*Attest:*

STEPHEN G. KUNIN

*Attesting Officer*   *Acting Commissioner of Patents and Trademarks*